(12) United States Patent
Holzer

(10) Patent No.: US 11,000,676 B2
(45) Date of Patent: May 11, 2021

(54) GUIDE FOR INTRAVASCULAR DEVICE

(71) Applicant: Asher Holzer, Ra'anana (IL)

(72) Inventor: Asher Holzer, Ra'anana (IL)

( * ) Notice: Subject to any disclaimer, the term of this patent is extended or adjusted under 35 U.S.C. 154(b) by 1537 days.

(21) Appl. No.: 14/426,766

(22) PCT Filed: Aug. 20, 2013

(86) PCT No.: PCT/IB2013/056747
§ 371 (c)(1),
(2) Date: Mar. 9, 2015

(87) PCT Pub. No.: WO2014/037836
PCT Pub. Date: Mar. 13, 2014

(65) Prior Publication Data
US 2015/0246209 A1    Sep. 3, 2015

Related U.S. Application Data

(60) Provisional application No. 61/696,321, filed on Sep. 4, 2012.

(51) Int. Cl.
*A61M 25/06* (2006.01)
*A61M 25/01* (2006.01)
*A61M 25/00* (2006.01)

(52) U.S. Cl.
CPC .... *A61M 25/0662* (2013.01); *A61M 25/0068* (2013.01); *A61M 25/0102* (2013.01); *A61M 25/0113* (2013.01); *A61M 2025/0188* (2013.01)

(58) Field of Classification Search
CPC .......... A61M 25/0662; A61M 25/0068; A61M 25/0102; A61M 25/0113; A61M 2025/0188; A61M 25/01; A61B 18/1492; A61B 2018/00577
See application file for complete search history.

(56) References Cited

U.S. PATENT DOCUMENTS

| 4,957,479 A | * | 9/1990 | Roemer ................... A61F 2/94 604/540 |
| 5,713,868 A | * | 2/1998 | Fussman ........... A61M 25/0662 604/164.01 |
| 7,758,625 B2 | | 7/2010 | Wu et al. |
| 8,048,032 B2 | * | 11/2011 | Root ................. A61M 25/0026 604/164.1 |

(Continued)

FOREIGN PATENT DOCUMENTS

WO    2006113863 A2    10/2006

OTHER PUBLICATIONS

"Hemicylindrical", 2020, www.lexico.com/en/definition/hemicylindrical (Year: 2020).*

(Continued)

*Primary Examiner* — Nathan R Price
*Assistant Examiner* — Weng Lee
(74) *Attorney, Agent, or Firm* — Kligler & Associates Patent Attorneys Ltd

(57) ABSTRACT

A device guide (30, 40, 50, 60, 70, 80, 90, 100, 110, 120, 130) includes a distal portion configured for insertion through a guide catheter (20) into a blood vessel (24) and having a semi-tubular shape chosen so as to guide an intravascular device (32) inserted through the guide catheter into the blood vessel.

9 Claims, 5 Drawing Sheets

(56) References Cited

U.S. PATENT DOCUMENTS

| | | | |
|---|---|---|---|
| 2003/0120267 A1* | 6/2003 | Kaufman | A61M 25/0041 606/14 |
| 2005/0085841 A1* | 4/2005 | Eversull | A61B 17/3431 606/190 |
| 2006/0259118 A1* | 11/2006 | Pal | A61F 2/95 623/1.11 |
| 2008/0097293 A1* | 4/2008 | Chin | A61B 1/0055 604/95.04 |
| 2014/0012281 A1* | 1/2014 | Wang | A61M 25/0023 606/108 |
| 2014/0018773 A1* | 1/2014 | Wang | A61M 25/0069 604/510 |

OTHER PUBLICATIONS

Vascular Solutions, Inc, "Guide liner Catheter: Coaxial guide extension with rapid exchange convenience", 4 pages, Oct. 8, 2010.
International Application # PCT/IB2013/056747 Search Report dated Dec. 30, 2013.

* cited by examiner

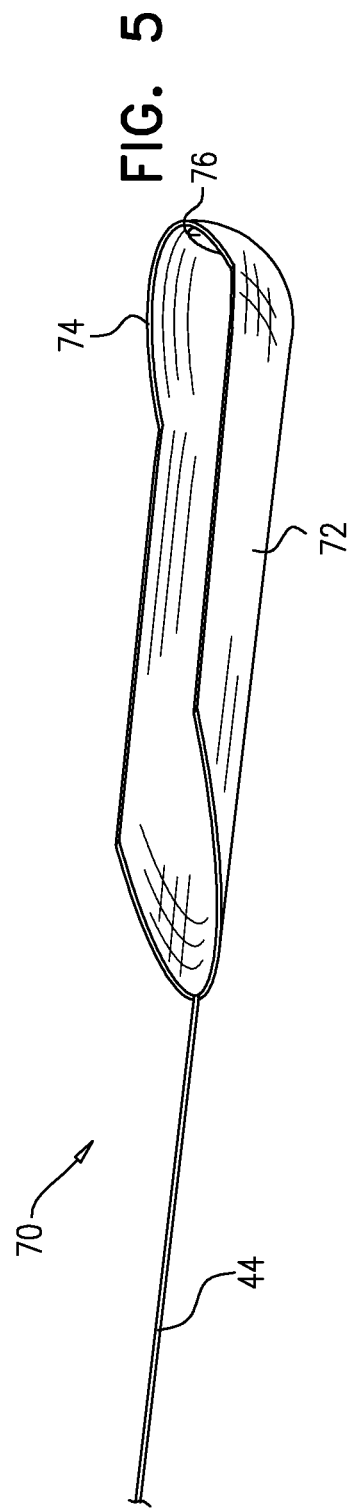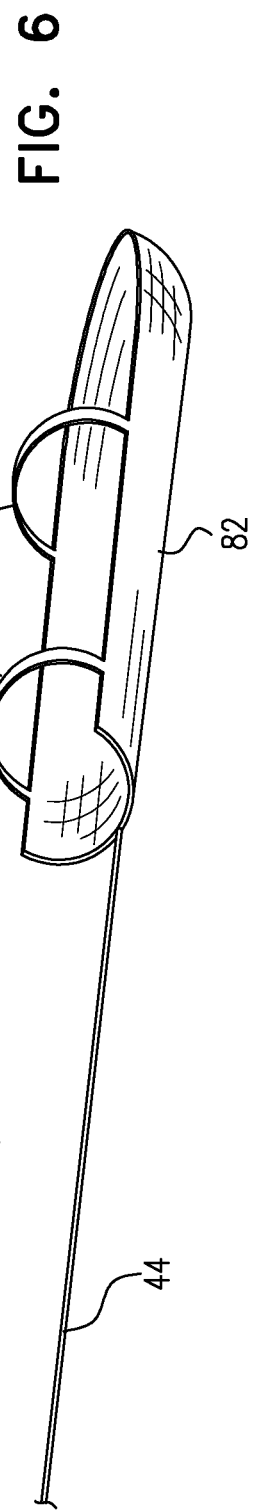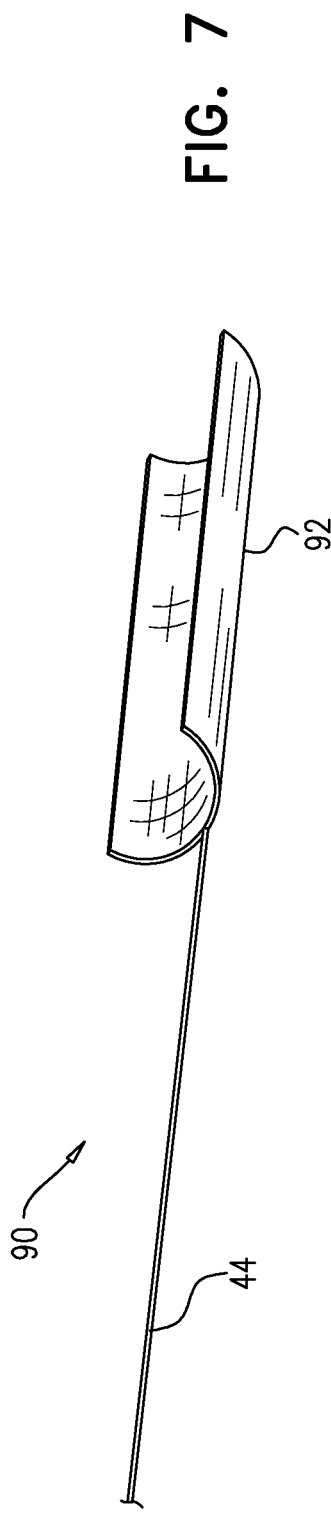

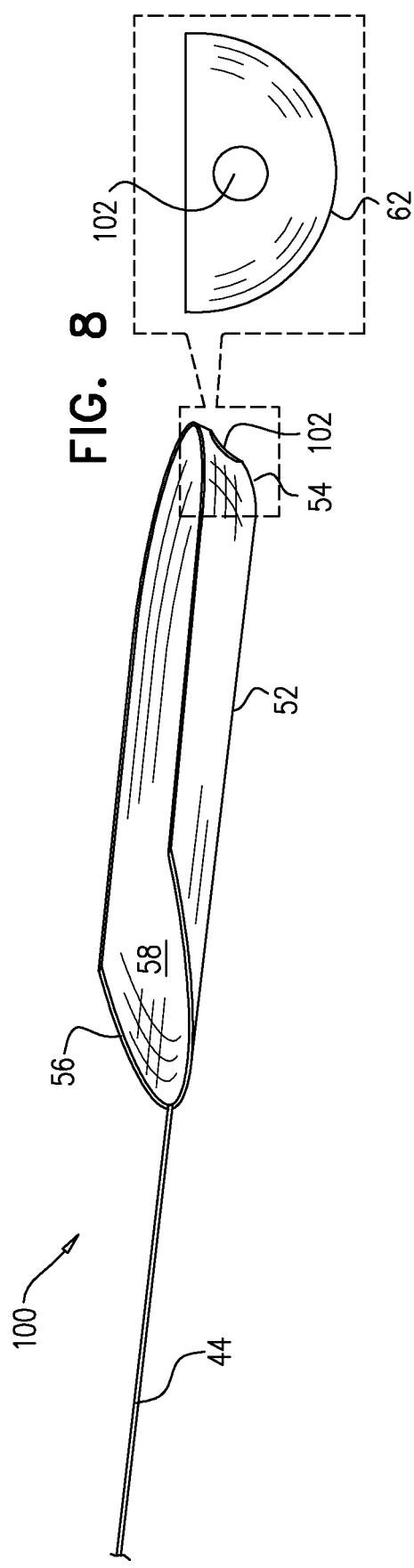
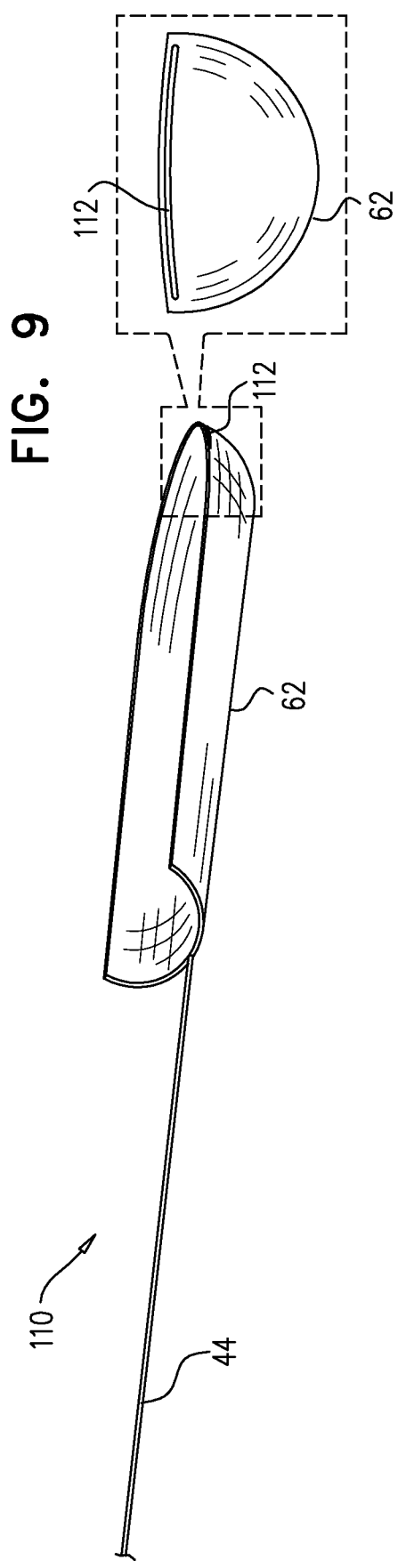

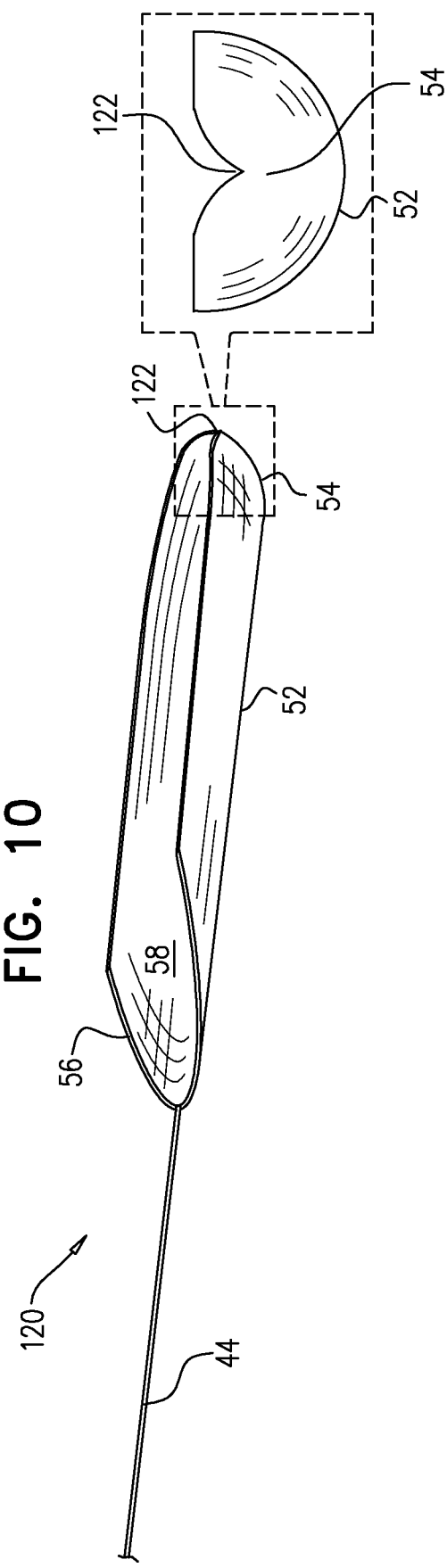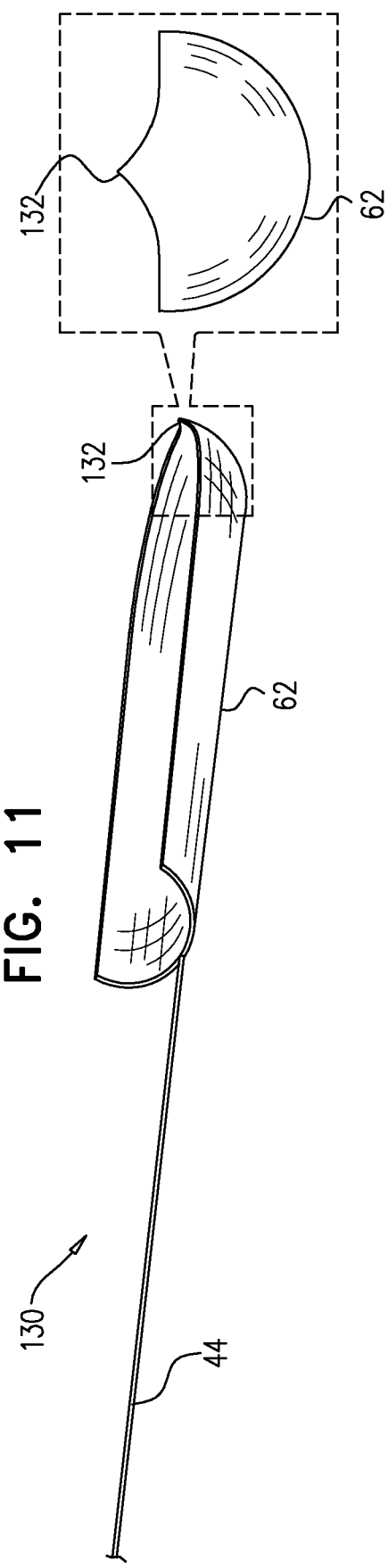

GUIDE FOR INTRAVASCULAR DEVICE

CROSS-REFERENCE TO RELATED APPLICATION

This application claims the benefit of U.S. Provisional Patent Application 61/696,321, filed Sep. 4, 2012, which is incorporated herein by reference.

FIELD OF THE INVENTION

The present invention relates generally to interventional cardiology, and particularly to implements that may be used in such procedures to facilitate insertion of intravascular devices into blood vessels.

BACKGROUND

Interventional cardiology procedures often require guidewires, catheters, and other instruments to be inserted into coronary arteries that branch off from the aorta. In such procedures, a guide catheter is typically inserted through the aorta and positioned alongside the ostium of the coronary artery that is to be treated. A guidewire is inserted through the guide catheter and into the coronary artery to the treatment site. At this point a balloon catheter (with or without a stent) is typically introduced over the guidewire into the treated lesion.

When the coronary artery is tightly curved and/or narrowed due to occlusion, stenosis, or torosity, for example, the balloon catheter may encounter resistance as it is inserted. As the cardiologist attempts to push the balloon catheter into the artery under these conditions, the balloon catheter exerts backward force on the guide catheter, and this force may be sufficient to dislodge the guide catheter from the ostium. Similar difficulties may be encountered in insertion of the guidewire. This sort of occurrence can make it difficult or impossible for the cardiologist to complete the procedure.

A number of solutions are known in the art for overcoming this problem of backward force and the difficulty of inserting a balloon catheter (or any other device) into a side branch due to unfavorable geometry.

For example, U.S. Pat. No. 8,048,032, whose disclosure is incorporated herein by reference, describes a coaxial guide catheter for interventional cardiology procedures. The coaxial guide catheter is passed through the lumen of a guide catheter and is extended beyond the distal end of the guide catheter and inserted into a branch artery. An interventional cardiology device is passed through the lumen of the coaxial guide catheter into the branch artery. This coaxial guide catheter is said to assist in resisting axial and shear forces exerted by the interventional cardiology device that would otherwise tend to dislodge the guide catheter from the branch artery.

SUMMARY

Embodiments of the present invention that are described hereinbelow provide improved devices and methods for guiding and insertion of invasive devices through curved lumens.

There is therefore provided, in accordance with an embodiment of the present invention, a device guide, including a distal portion configured for insertion through a guide catheter into a blood vessel and having a semi-tubular shape chosen so as to guide an intravascular device inserted through the guide catheter into the blood vessel.

Typically, the device guide includes an insertion rod, which is connected to a proximal end of the distal portion and is configured to push the distal portion of the device guide through the guide catheter.

In one embodiment, the distal portion includes a tube, which has a longitudinal cut and is configured to open along the longitudinal cut.

In other embodiments, the distal portion has a hemi-cylindrical form. Typically, the hemi-cylindrical form is closed around no more than 180° of a circumference of the hemi-cylindrical form. The distal portion may include a rounded distal tip. Additionally or alternatively, the distal portion may include one or more flexible rings extending over an open side of the distal portion.

In some embodiments, the distal portion includes a canted proximal end. Additionally or alternatively, the distal portion has a hole in a distal end thereof, configured for passage of the intravascular device through the hole, or a slit in a distal end thereof.

Further alternatively, the distal portion includes an upward-pointing or downward-pointing beak at a distal tip of the distal portion.

There is also provided, in accordance with an embodiment of the present invention, a method for performing an intravascular procedure, which includes inserting a guide catheter into a blood vessel. A device guide is passed through the guide catheter so that a distal portion of the device guide, having a semi-tubular shape, protrudes from a distal end of the guide catheter into the blood vessel. An intravascular device is inserted through the guide catheter via the distal portion of the device guide to a target site in the blood vessel.

In a disclosed embodiment, the semi-tubular shape defines a radial opening extending along the distal portion, and passing the device guide includes rotating the device guide so that the radial opening faces toward the target site, whereby the intravascular device exits the device guide toward the target site via the radial opening. Alternatively, the distal portion has a hole in a distal end thereof, and inserting the intravascular device includes passing the intravascular device through the hole.

In some embodiments, passing the device guide includes inserting the device guide into a curve of the blood vessel, whereby the intravascular device passes through the curve, via the device guide, toward the target site. In one embodiment, inserting the guide catheter includes advancing a distal end of the guide catheter into an ostium of a coronary artery, and passing the device guide includes advancing the distal portion of the device guide out of the distal end of the guide catheter into the coronary artery. Typically, inserting the intravascular device includes passing a guidewire through the distal portion of the device guide toward an occlusion in the coronary artery.

The present invention will be more fully understood from the following detailed description of the embodiments thereof, taken together with the drawings in which:

BRIEF DESCRIPTION OF THE DRAWINGS

FIGS. 2-11 are schematic, pictorial illustrations of device guides, in accordance with various embodiments of the present invention.

DETAILED DESCRIPTION OF EMBODIMENTS

Figure 1:
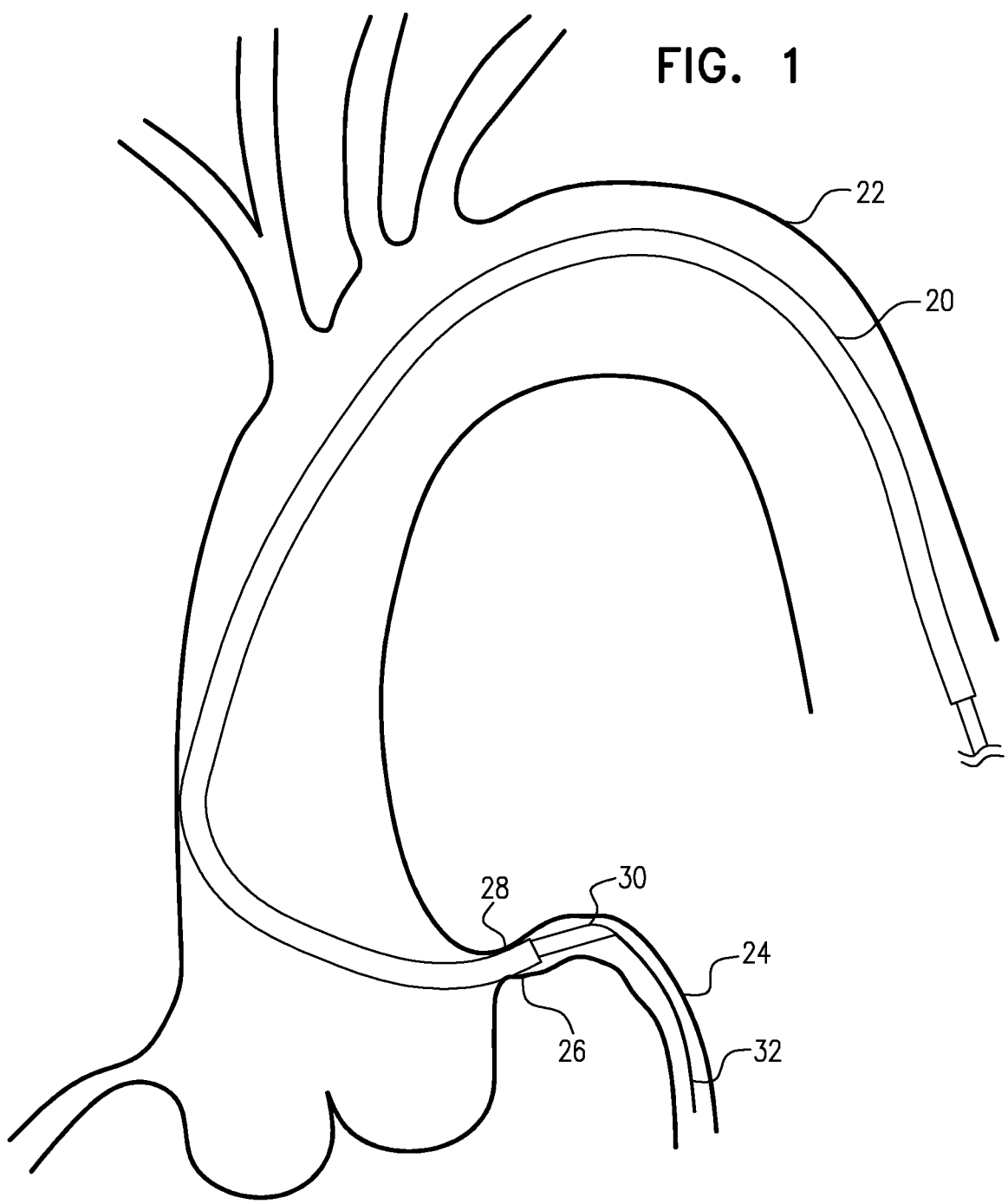
FIG. 1 is a schematic sectional view of a portion of a patient's vascular system, illustrating the deployment and use of a device guide for an intravascular device, in accordance with an embodiment of the present invention.

Embodiments of the present invention that are described hereinbelow provide solutions to the problems that are encountered in insertion of invasive device through tightly-curved and narrow lumens. These solutions are particularly effective in vascular catheterization, and certain embodiments are described below with reference particularly to catheterization of the coronary arteries. The principles of the present invention, however, may alternatively be applied in invasive procedures involving other sorts of physiological lumens.

In the disclosed embodiments, a device guide is inserted through a main guide catheter and is extended out of the distal end of the guide catheter into a branch artery, such as a coronary artery. The distal portion of the device guide has a radial opening extending along the length of the distal portion. A guide wire, treatment catheter or other device is then inserted through the guide catheter and passes out into the branch artery via the device guide, typically through the radial opening of the distal portion of the device guide.

For example, in some embodiments the distal portion of the guide may have a semi-tubular form. The term "semi-tubular," as used in the context of the present patent application, means a shape defined by cutting away a longitudinal section of a hollow, cylindrical tube. One example of a semi-tubular from is a hemi-cylinder, with a circumferential extent of 180°, but other semi-tubular forms, of greater or smaller circumferential extent and shapes that are not strictly cylindrical in profile, may similarly be used in embodiments of the present invention.

This design of the device guide is advantageous in that the guide occupies relatively little space in the lumen of the guide catheter and when extended into the coronary arteries—roughly half the space occupied by a cylindrical guide of similar dimensions. Therefore, by comparison with solutions known in the art, this sort of device guide enables the cardiologist to insert intravascular devices of relatively greater diameter through the guide catheter and through the device guide and with greater ease. Furthermore, the opening of the distal portion of the device guide may be rotated so that devices passed through the guide enter curved arteries in the desired direction.

Furthermore, the shape of the device guide makes it possible to locate the device guide at some distance outside a side branch into which an intravascular device is to be inserted, and still permit the device to be inserted via the open side of the device guide. This option is generally not feasible when tubular extensions of the guide catheter are used.

In addition, the semi-tubular shape of the device guide allows blood to freely flow into a coronary artery in which the device guide is placed (whereas tubular extensions may block the artery). Freer blood flow reduces the risk of turbulence, which may lead to clotting, and also reduces or eliminates angina and risks of possible arrhythmias due to lack of blood flow into the coronaries.

FIG. 1 is a schematic sectional view of a portion of a patient's vascular system, illustrating the deployment and use of a device guide 30 for an intravascular device, in accordance with an embodiment of the present invention. A guide catheter 20 is inserted through an aortic arch 22 of the patient, and manipulated so that a distal end 26 of catheter 20 lodges in an ostium 28 of a coronary artery 24. Guide 30 (whose design is described with reference to the figures that follow) is inserted through the lumen of guide catheter 20 so that the distal portion of the device guide protrudes out of the distal end of the guide catheter into artery 24.

An intravascular device 32, such as a guidewire and/or treatment catheter, is then passed through catheter 20 and through guide 30 to a treatment site in artery 24. Guide 30 has a semi-tubular shape, with an opening extending along its length, and may be rotated so that this open side faces in the desired direction relative to the curvature of artery 24 (i.e., downward in the view shown in FIG. 1) and/or relative to other anatomical features. As shown in the figure, guide 30 assists in proper insertion of device 32 (including a catheter device that may be inserted via the guide) and reduces backward force on distal end 26 of catheter 20. As guide 30 is more rigid than a guidewire, it provides better resistance to backward force that may be exerted by lesions in artery 24.

The figures that follow show a range of possible designs of guide 30, in accordance with various embodiments of the present invention. These designs are shown by way of example and not limitation. For the sake of clarity, each guide is marked with a different indicator number, but any of them may take the place of guide 30 in the embodiment shown in FIG. 1. Furthermore, these guides may be used not only in the sort of procedure that is illustrated in FIG. 1, but also in other sorts of intravascular therapeutic and diagnostic procedures that are known in the art.

Figure 2:
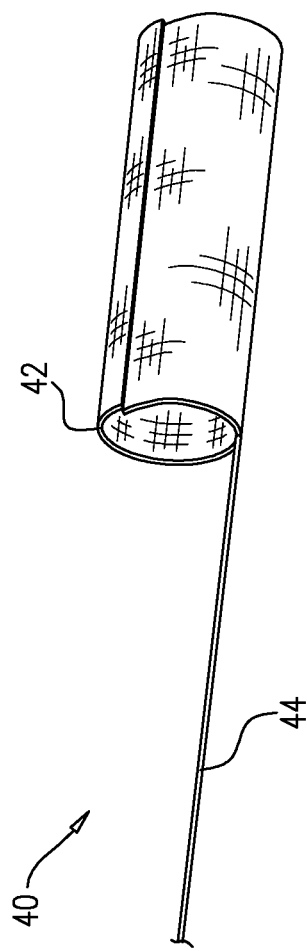

FIG. 2 is a schematic, pictorial illustration of a device guide 40, in accordance with an embodiment of the present invention. A distal portion 42 of guide 40 comprises a tube, which opens along a longitudinal cut. Distal portion 42 (as well as the distal portions of the other device guides described below) typically comprises a thin shell made from a suitable biocompatible polymer or metal, or a polymer-coated metal, or a polymer with reinforced internal braided metal mesh.

Distal portion 42 is connected at its proximal end to an insertion rod 44, which is used to push the distal portion of guide 40 through guide catheter 20. (The other device guides shown below have similar insertion rods.) Rod 44 typically comprises a semi-rigid, kink-resistant resilient strip, made from a suitable biocompatible metal, such as stainless steel 302. This geometry enables the use of "rapid exchange" delivery systems and techniques, as well as "over the wire" techniques. Distal portion 42 is typically 20 mm long and has an outer diameter in the range of 1.7-2.3 mm. The overall length of device guide 40 may be on the order of 145 cm. Other lengths and diameters are possible, depending on the anatomy of the treated lumen.

Figure 3:
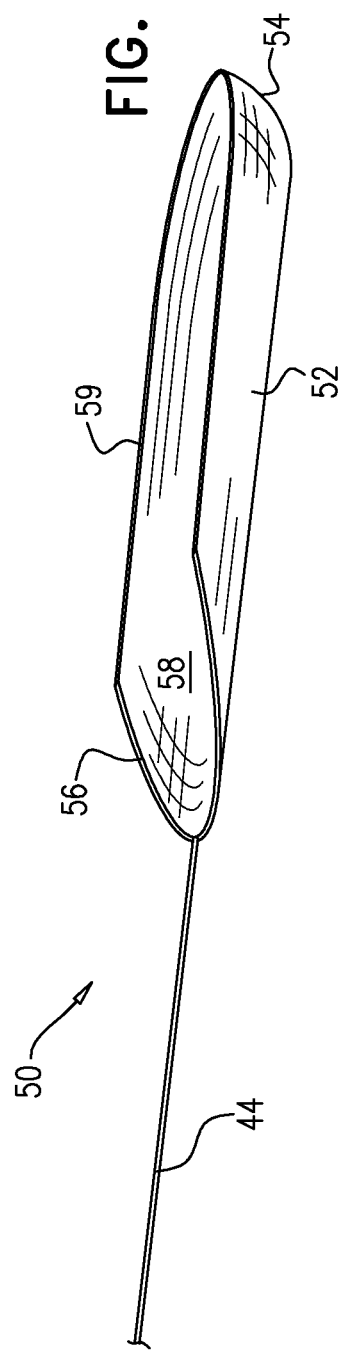

FIG. 3 is a schematic, pictorial illustration of a device guide 50, in accordance with another embodiment of the present invention. A distal portion 52 of guide 50 has a hemi-cylindrical form, with an inner cavity 58 that opens radially upward in the pictured view. Although cavity 58 in distal portion 52 is shown in the figure as being closed around roughly 180° of its circumference, in alternative embodiments (not shown in the figures), the circumferential extent of the distal portion may be larger or smaller. (A smaller circumferential extent may allow devices of larger diameter to be inserted through the device guide.) A distal tip 54 of distal portion 52 is rounded to prevent damage to vessel walls and to assist in guiding inserted devices in the proper direction. Other shapes of the distal tip may alternatively be used, as shown in other figures. A proximal end 56 of distal portion 52 is canted to facilitate retraction of guide 50 through the guide catheter. An edge 59 of cavity 58 may be rounded to avoid any possible damage to the blood vessel lumen.

Radiopaque markers, containing metal of high atomic number, for example (not shown in the figure), may be embedded in guide 50 to facilitate visualization under X-ray imaging. These markers may be located in the distal part, proximal part, and/or along the length of device guide 50 in order both to locate the distal part and to indicate its orientation in three dimensions.

Figure 4:
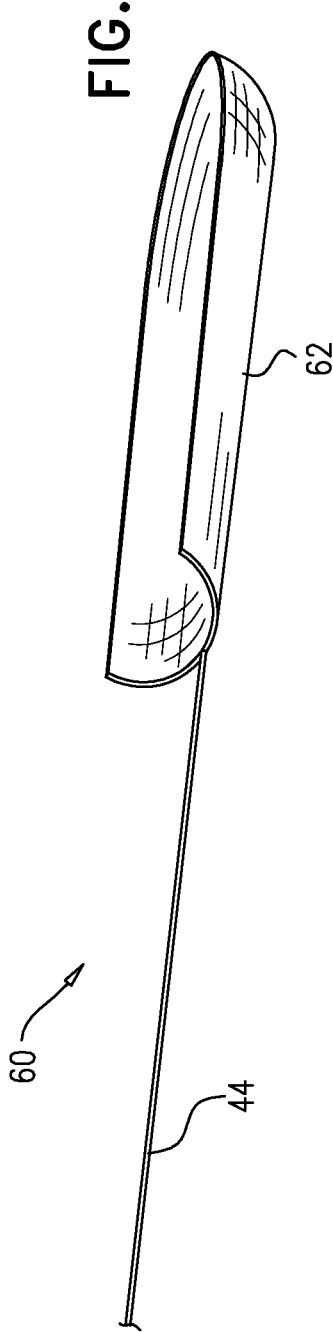

FIG. 4 is a schematic, pictorial illustration of a device guide 60, in accordance with yet another embodiment of the present invention. A distal portion 62 of guide 60 has a rounded hemi-cylindrical form, like guide 50, but without the canted proximal end.

FIG. 5 is a schematic, pictorial illustration of a device guide 70, in accordance with still another embodiment of the present invention. A distal portion 72 of guide 70 has a hemi-cylindrical form with a rounded distal end 74 to prevent damage to vessel walls. In this embodiment, however, there is a hole 76 in distal end 74, through which a guidewire and/or a balloon catheter may be passed into the blood vessel.

FIG. 6 is a schematic, pictorial illustration of a device guide 80, in accordance with a further embodiment of the present invention. A distal portion 82 of guide 80 again has a hemi-cylindrical form, as in the preceding embodiments, but in this case one or more flexible rings extend over the open side of the distal portion. These rings are useful particularly when guide 80 is to be inserted into a blood vessel over a guidewire that is already in place: The guidewire passes through the rings as the guide is advanced through the vessel. Similar sorts of rings may be added to the designs described above.

FIG. 7 is a schematic, pictorial illustration of a device guide 90, in accordance with an additional embodiment of the present invention. In this case, distal portion 92 of guide 90 has a simple hemi-cylindrical form. The corners of the distal portion may be rounded to avoid injury to blood vessels.

FIG. 8 is a schematic, pictorial illustration of a device guide 100, in accordance with another embodiment of the present invention. In this case, distal portion 52 of guide 100 has a hole 102, similar to that in the embodiment of FIG. 5.

FIG. 9 is a schematic, pictorial illustration of a device guide 110, in accordance with an additional embodiment of the present invention. Here, distal portion 62 of guide 110 has a slit 112, which may serve a purpose similar to that of hole 102.

FIG. 10 is a schematic, pictorial illustration of a device guide 120, in accordance with a further embodiment of the present invention. In this case, distal portion of guide 120 has a downward-pointing "beak" 122 at distal tip 54.

FIG. 11 is a schematic, pictorial illustration of a device guide 130, in accordance with still another embodiment of the present invention. In this case, distal portion 62 of guide 130 has an upward-pointing "beak" 132 at its distal tip.

The use of an upward- or downward-pointing beak, with or without hole 102 (as in FIG. 8), may help in guiding insertion of a balloon catheter or other device by aiming it in the desired direction.

Various methods can be used to produce the sorts of devices that are described above. For example, laser micro-cutting can be used to cut a metal or plastic tube to create the desired semi-tubular shape. Cuts, such as radial slits, may also be made within the device to enhance flexibility in certain segments or to permit insertion of radiopaque markers. After cutting, the tube may be overmolded with an elastic polymer.

Alternatively, a flexible wire, such as a Nitinol wire having a diameter in the range of 0.15-0.6 mm, for instance, may be formed and set in the desired shape of the device, for example bent in a curved, zigzag pattern that defines the desired shape. The wire may then be overmolded with an elastic polymer to create the final, smooth shape.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. A device guide, comprising a distal portion configured for insertion through a guide catheter into a blood vessel and having a semi-tubular shape chosen so as to guide an intravascular device inserted through the guide catheter into the blood vessel,
   wherein the distal portion has a hemi-cylindrical form, and wherein the distal portion comprises one or more flexible rings extending over an open side of the distal portion.

2. The device guide according to claim 1, comprising an insertion rod, which is connected to a proximal end of the distal portion, wherein the insertion rod is configured to push the distal portion of the device guide through the guide catheter.

3. The device guide according to claim 1, wherein the hemi-cylindrical form is closed around no more than 180° of a circumference of the hemi-cylindrical form.

4. The device guide according to claim 1, wherein the distal portion comprises a rounded distal tip.

5. The device guide according to claim 1, wherein the distal portion comprises a canted proximal end.

6. The device guide according to claim 1, wherein the distal portion has a hole in a distal end thereof, configured for passage of the intravascular device through the hole.

7. The device guide according to claim 1, wherein the distal portion has a slit in a distal end thereof.

8. The device guide according to claim 1, wherein the distal portion comprises an upward-pointing beak at a distal tip of the distal portion.

9. The device guide according to claim 1, wherein the distal portion comprises a downward-pointing beak at a distal tip of the distal portion.

\* \* \* \* \*